(12) United States Patent
Inoue et al.

(10) Patent No.: US 6,608,921 B1
(45) Date of Patent: Aug. 19, 2003

(54) INSPECTION OF SOLDER BUMP LIGHTED WITH RAYS OF LIGHT INTERSECTING AT PREDETERMINED ANGLE

(75) Inventors: Masahiko Inoue, Tokyo (JP); Hiroshi Ikeda, Kanagawa (JP)

(73) Assignee: NEC Electronics Corporation, Kanagawa (JP)

( * ) Notice: Subject to any disclaimer, the term of this patent is extended or adjusted under 35 U.S.C. 154(b) by 0 days.

(21) Appl. No.: 09/378,035

(22) Filed: Aug. 20, 1999

(30) Foreign Application Priority Data

Aug. 21, 1998 (JP) .......................................... 10-235940

(51) Int. Cl.[7] .............................................. G06K 9/00
(52) U.S. Cl. ........................ 382/146; 382/150; 382/190
(58) Field of Search ................................ 382/108, 147, 382/149, 172, 150, 225, 190, 146; 348/126, 131; 356/237.5; 361/760; 250/559.34; 358/471, 484

(56) References Cited

U.S. PATENT DOCUMENTS

| | | | | |
|---|---|---|---|---|
| 4,688,939 A | * | 8/1987 | Ray ........................ | 356/237.5 |
| 4,942,481 A | * | 7/1990 | Yoshinouchi et al. ....... | 358/471 |
| 5,023,917 A | * | 6/1991 | Bose et al. .................. | 382/149 |
| 5,058,178 A | * | 10/1991 | Ray ........................... | 348/126 |
| 5,060,065 A | * | 10/1991 | Wasserman .................. | 382/147 |
| 5,113,565 A | * | 5/1992 | Cipolla et al. ............... | 228/102 |
| 5,761,337 A | * | 6/1998 | Nishimura et al. ......... | 382/150 |
| 5,984,165 A | * | 11/1999 | Inoue et al. ................. | 228/234 |
| 6,125,043 A | * | 9/2000 | Hauer et al. ................ | 361/760 |

FOREIGN PATENT DOCUMENTS

| | | |
|---|---|---|
| JP | 58-44849 | 9/1956 |
| JP | S56-140315 | 9/1956 |
| JP | 49-29856 | 3/1974 |
| JP | 60-154143 | 8/1985 |
| JP | 2-110306 | 4/1990 |
| JP | 2-150704 | 6/1990 |
| JP | 5-8458 | 2/1993 |
| JP | 5-149726 | 6/1993 |
| JP | 6-88709 | 3/1994 |
| JP | H6-88709 | 3/1994 |
| JP | 7-283521 | 10/1995 |
| JP | 8-147468 | 6/1996 |
| JP | 8-159719 | 6/1996 |
| JP | H9-159719 | 6/1996 |
| JP | H9-311020 | 2/1997 |
| JP | H9-232373 | 9/1997 |
| JP | H9-236415 | 9/1997 |
| JP | 9-311020 | 12/1997 |
| JP | 10-90191 | 4/1998 |
| JP | H8-10-122828 | 5/1998 |
| JP | 10-185528 | 7/1998 |

\* cited by examiner

Primary Examiner—Timothy M. Johnson
Assistant Examiner—Sheela Chawan
(74) Attorney, Agent, or Firm—Scully, Scott, Murphy & Presser (57) ABSTRACT

A bump inspecting apparatus lights a spherical solder bump mounted on the surface of a circuit board and has a reinforcing resin applied to the lower half thereof from all circumferential directions with rays of light which intersect at a predetermined angle. An image of the lighted solder bump is captured while the amount of light irradiated upon the central portion of a solder bump is reduced. An object is extracted from image data obtained by the image capture and the area and/or the aspect ratio of the object are confirmed. The quality of the state of the reinforcing resin applied to the solder bump can be inspected.

7 Claims, 8 Drawing Sheets

INSPECTION OF SOLDER BUMP LIGHTED WITH RAYS OF LIGHT INTERSECTING AT PREDETERMINED ANGLE

BACKGROUND OF THE INVENTION

1. Field of the Invention

This invention relates to a method and an apparatus for lighting a solder bump on a BGA (Ball Grid Array) board, and more particularly to a method and an apparatus for lighting and inspecting a solder bump.

2. Description of the Related Art

A circuit board wherein spherical solder bumps are mounted on the surfaces of connection pads in order to mount a circuit chip on the surface of the circuit board is available at present and normally called BGA board. A circuit board of the type described, however, sometimes suffers from peeling off of a solder bump during working, and this gives rise to failure in connection of a circuit chip mounted on the surface of the circuit board.

In order to solve the problem described, another BGA board has been proposed wherein a reinforcing resin is applied to a solder bump after the solder bump is attached to the surface of the board so that a lower half of the solder bump is held to the board by the reinforcing resin. The BGA board prevents peeling off of the solder bump from the circuit board during working because the connection between the solder bump and the circuit board is reinforced by the reinforcing resin.

However, since the reinforcing resin is an insulator, if it is applied up to an upper portion of a solder bump, then this causes failure in connection of a circuit chip mounted on the surface of the circuit board. Therefore, it is necessary to inspect a condition of the reinforcing resin applied to a solder bump, and an effective technique for inspecting has not been developed.

A possible solution, for example, would be to use visual inspection to inspect the condition of a reinforcing resin applied to a solder bump. In recent years, however, solder bumps are smaller in size and mounted at a higher density, and it is not practical to inspect a large number of solder bumps of BGA boards produced in a mass by visual inspection.

For example, Japanese Patent Laid-Open Publication No. 311020/1997 and Japanese Patent Laid-Open Publication No. 147467/1996 disclose a method of and an apparatus for inspecting the outside shape of a solder bump. Although the method and apparatus allows inspection of an outside shape of a solder bump, it does not allow inspection of the condition of a reinforcing resin applied to a solder bump.

SUMMARY OF THE INVENTION

It is an object of the present invention to provide a bump lighting method and apparatus which lights a solder bump so that the condition of a reinforcing resin which has been applied can be inspected well.

It is another object of the present invention to provide a bump image capturing method and apparatus which captures an image of a solder bump so that the condition of a reinforcing resin which has been applied can be inspected well.

It is a further object of the present invention to provide an image processing method and apparatus which determines from image data of a solder bump whether the condition of an applied reinforcing resin is good or bad.

It is still a further object of the present invention to provide a bump inspecting method and apparatus which inspects the condition of a reinforcing resin applied to a solder bump well.

It is yet a further object of the present invention to provide an information storage medium to store a program for enabling a computer to execute a determination from image data of a solder bump whether the condition of an applied reinforcing resin is good or bad is stored as software.

The bump lighting apparatus according to the present invention lights a spherical solder bump having a reinforcing resin applied to the lower half mounted on the surface of a circuit board and comprises a board holding mechanism for holding the circuit board at a predetermined position, and an irradiating mechanism for irradiating rays of light upon the outer periphery of a solder bump from all circumferential directions such that the rays of light may intersect at a predetermined angle with the surface of the circuit board held by the board holding mechanism.

Accordingly, in the bump lighting apparatus, the rays of light which intersect at the predetermined angle with the surface of the circuit board held at the predetermined position by the board holding mechanism are irradiated from all circumferential directions upon the outer periphery of the solder bump by the irradiating mechanism. Since the position of the boundary between the upper half of the spherical solder bump and the reinforcing resin can be lighted substantially uniformly, the bump lighting apparatus can light the solder bump and the reinforcing resin well for distinguishing them from each other.

In the bump lighting apparatus, the irradiating mechanism may include a plurality of light-emitting devices for individually emitting rays of light, and a light source holding mechanism for holding the light-emitting devices in an inwardly radially directed condition so that the rays of light emitted from the light-emitting devices may be concentrated at a point.

In this case, the plurality of light-emitting devices are disposed in an inwardly radially directed condition by the light source holding mechanism, and the rays of light individually emitted from the light-emitting devices are concentrated upon the one point. Consequently, the rays of light are irradiated upon the outer periphery of the solder bump from all circumferential directions. The irradiating mechanism which irradiates the rays of light in this manner can be implemented with a simple structure of a small number of parts.

In the bump lighting apparatus, the irradiating mechanism may include a plurality of light-emitting devices for individually emitting rays of light, a light source holding mechanism for holding the light-emitting devices in a circular fashion, and a light diverting mechanism for diverting the rays of light emitted from the light-emitting devices arranged on the light source holding mechanism so that the rays of light may be concentrated at a point.

In this case, the plurality of light-emitting devices are disposed in a circular fashion by the light source holding mechanism, and the rays of light individually emitted from the light-emitting devices are diverted in predetermined directions and concentrated at one point by the light converting mechanism. Consequently, the rays of light are irradiated upon the outer periphery of the solder bump from all circumferential directions by the irradiating mechanism. The irradiating mechanism which irradiates the rays of light in this manner can be formed in a structure which allows easy disposition of the light-emitting devices.

The bump lighting apparatus may further comprise a light converting member for converting the rays of light to be irradiated upon the solder bump into polarized light. In this case, since the rays of light to be irradiated upon the solder bump are converted into polarized light by the light converting member, reflected light from a solder bump with a mirror surface can be prevented from having an extremely high intensity.

In the bump lighting apparatus, the light-emitting devices may emit rays of light of a color substantially complementary to the coloring of the reinforcing resin. In this case, since the rays of light to be irradiated upon the solder bump from the light-emitting devices has a substantially complementary color to the coloring of the reinforcing resin, the rays of light are reflected well from the solder bump whose surface is formed as a mirror surface, and the reinforcing resin absorbs most of the rays of light irradiated thereupon. Accordingly, the bump lighting apparatus can light a solder bump and the reinforcing resin for distinguishing them well from each other.

The bump image capturing apparatus according to the present invention capture an image of a spherical solder bump having a reinforcing resin applied to the lower half, mounted on the surface of a circuit board and comprises a bump lighting apparatus for holding the circuit board at a predetermined position to light the solder bump, an image capture apparatus for capturing an image of reflected light from the solder bump lighted by the bump lighting apparatus from a direction perpendicular to the surface of the circuit board, and an intensity adjusting mechanism for lowering the intensity of the light reflected from the central portion of a solder bump within the image capture range of the image capture apparatus.

Consequently, according to the method for capturing a bump image by the capturing apparatus of the present invention, the circuit board is held at a predetermined position and the solder bump is lighted by the bump lighting apparatus, and the image of reflected light from the lighted solder bump is captured from the direction perpendicular to the surface of the circuit board image capture apparatus. However, since the intensity of the reflected light from the central portion of a solder bump in the image capture range of the image capture apparatus is lowered by the intensity adjusting mechanism, the intensity of the rays of light reflected from the top portion of the solder bump whose surface is formed as a mirror surface is lowered to a level suitably capturing with which the rays of light. Consequently, an image of a solder bump likely to reflect light intensity from the top portion can be captured well without suffering from exposure to excessive light.

In the bump image capturing apparatus, the intensity adjusting mechanism may include an optical filter having a transmittivity which with a concentrical variation which decrease toward the center, and a filter disposing mechanism for disposing the optical filter in the gap between the image capture apparatus and the solder bump.

In this case, since the optical filter is disposed in the gap between the image capture apparatus and the solder bump by the filter disposing mechanism and the optical filter has a transmittivity which toward the center decreases concentrically, the intensity of reflected light from the central portion of a solder bump in the image capture range of the image capture apparatus can be lowered with certainty with a simple structure by the intensity adjusting mechanism.

In the bump image capturing apparatus, the intensity adjusting mechanism may adjust the intensity of the light reflected from the solder bump to be imaged to the dynamic range of the image capture apparatus. In this case, since the intensity of the light reflected from the solder bump to be imaged is adjusted to the dynamic range of the image capture apparatus by the intensity adjusting mechanism, the image capture apparatus can capture an image of the solder bump in a condition of good light exposure. Another bump image capturing apparatus is applied to capture an image of a spherical solder bump having a reinforcing resin applied to the lower half, mounted on the surface of a circuit board and comprises a bump lighting apparatus for holding the circuit board at a predetermined position to light the solder bump, an image capture apparatus for capturing an image of reflected light from the solder bump lighted by the bump lighting apparatus from a direction perpendicular to the surface of the circuit board, a first light converting member for converting the light upon the solder bump irradiated by the bump lighting apparatus into polarized light, and a second light converting member for converting the light reflected from the solder bump and to be imaged by the image capture apparatus into polarized light.

Accordingly, in the bump image capturing apparatus according to the present invention, the circuit board is held at a predetermined position and the solder bump is lighted by the bump lighting apparatus, and an image of reflected light from the lighted solder bump is captured from a direction perpendicular to the surface of the circuit board by the image capture apparatus. However, the rays of light to be irradiated upon the solder bump from the bump lighting apparatus are converted into polarized light by the first light converting member, and the rays of light reflected from the solder bump and to be imaged by the image capture apparatus are converted into polarized light by the second light converting member. Consequently, the intensity of the rays of light reflected from the top portion of the solder bump is lowered to a level suitably capturing with which the rays of light, and an image of a solder bump likely to reflect light intensity from the top portion can be captured well without suffering from exposure to excessive light.

In the bump image capturing apparatus, the bump lighting apparatus may be the bump lighting apparatus according to the present invention described above.

In this case, the position of the boundary between the spherical solder bump and the reinforcing resin is lighted substantially uniformly from all circumferential directions by the bump lighting apparatus according to the present invention, and the image of the solder bump thus lighted is captured by the bump image capturing with the intensity of reflected light lowered at least at the top portion of the solder bump. Accordingly, the bump image capturing apparatus can capture an image of the solder bump and the reinforcing resin under condition in which they can be distinguished well from each other.

The image processing apparatus according to the present invention is applied to process image data of a spherical solder bump having a reinforcing resin applied to the lower half, mounted on the surface of a circuit board and comprises image converting means for converting the multilevel image data in binary form, object extracting means for extracting an object from the binary image data by the image converting means corresponding to the portion of a solder bump exposed above the reinforcing resin, and quality determining means for determining whether the object extracted by the object extracting means is good or bad.

Accordingly, in the image processing apparatus according to the present invention, the multilevel image data are converted in binary form by the image converting means, and an object corresponding to the portion of a solder bump exposed above the reinforcing resin is extracted from the binary image data by the object extracting means, and the quality of extracted object is determined by the quality determining means. Consequently, the quality of the state of the reinforcing resin applied to the solder bump can be determined. Because of no need to inspect a very large number of very small solder bumps by visual observation, the yield of circuit boards can be increased.

The image processing apparatus may further comprise range limiting means for limiting the processing range of image data to a circular shape corresponding to the outside shape of a solder bump. In this case, limitation of the processing range of the image data to a circular shape corresponding to the outside shape of the solder bump by the range limiting means, enables image data only of the portion of a solder bump necessary for determining the state of the reinforcing resin applied to the solder bump to be processed, and various image processes to be completed rapidly.

In the image processing apparatus, the image converting means may include average detecting means for detecting an average brightness of the image data in the circumferentially inward portion of the circle limited by the range limiting means, and threshold value calculating means for adding a predetermined offset value to the average brightness detected by the average detecting means to calculate a threshold value for conversion in binary form.

In this case, an average brightness of the image data in the circumferentially inward portion of the circle limited by the range limiting means is detected by the average detecting means, and the predetermined offset value is added to the average brightness by the threshold value calculating means to calculate a threshold value for conversion in binary form. Since the image converting means converts the multilevel image data in binary form with the threshold value, the image data can be converted in binary form so that the solder bump and the reinforcing resin are distinguished well from each other.

The image processing apparatus may be constructed such that it further comprises process controlling means for controlling at least the processing operation of the quality determining means, and that the object extracting means includes means for successively scanning the image data of one solder bump to successively extract a plurality of objects while the quality determining means includes means for successively inspecting the plurality of objects corresponding to the one solder bump, and the process controlling means includes means for completing the processing of the quality determining means at the point in time when one good object is detected from among the plurality of objects.

In this case, the image data of one solder bump are successively scanned by the object extracting means to successively extract a plurality of objects, and the plurality of objects corresponding to the one solder bump are successively inspected by the quality determining means. However, at the point in time when one good object is detected from among the plurality of objects, the processing of the quality determining means for the remaining objects is omitted by the process controlling means. Consequently, since the processing for the plurality of objects is limited to minimum necessary processing and unnecessary processing is not executed, the processing can be completed rapidly.

In the image processing apparatus, the object extracting means may extract one object from the image data at a central portion. In this case, since one object is extracted from the image data at a central portion by the object extracting means, the object of the portion of a solder bump exposed above the reinforcing resin can be extracted at one time, and this processing can be completed rapidly.

In the image processing apparatus, the quality determining means may include area detecting means for detecting the area of an object extracted by the object extracting means, and area comparing means for comparing the area detected by the area detecting means with a predetermined tolerance.

In this case, the area of the object extracted by the object extracting means is detected by the area detecting means, and the area is compared with the predetermined tolerance by the area comparing means. Consequently, since whether the area of an upper portion of the solder bump exposed above the reinforcing resin is suitable or not is determined by the quality determining means, the quality of the state of the reinforcing resin applied to the solder bump can be determined simply.

In the image processing apparatus, the quality determining means may include ratio detecting means for detecting the aspect ratio of the object extracted by the object extracting means, and ratio comparing means for comparing the aspect ratio detected by the ratio detecting means with a predetermined tolerance.

In this case, the aspect ratio of the object extracted by the object extracting means is detected by the ratio detecting means, and the aspect ratio is compared with the predetermined tolerance by the ratio comparing means. Consequently, since whether the shape of an upper portion of the solder bump exposed above the reinforcing resin is suitable or not is determined by the quality determining means, the quality of the state of the reinforcing resin applied to the solder bump can be determined simply.

In the image processing apparatus, the ratio detecting means may detect the major axis of the object extracted by the object extracting means and use the detected major axis of the object as a vertical axis.

In this case, the major axis of the object extracted by the object extracting means is detected by the ratio detecting means as a vertical axis, and the aspect ratio of the object is detected with respect to the vertical axis. Since the aspect ratio of the object can be detected as a ratio between the major axis and the minor axis, a deformed object due to noise can be prevented from being recognized in error as a substantially circular object of the exposed portion of a solder bump.

The bump inspecting apparatus according to the present invention comprises the bump image capturing apparatus and the image processing apparatus.

Accordingly, in the bump inspecting apparatus according to the present invention, the position of the boundary between the spherical solder bump and the reinforcing resin is lighted substantially uniformly from all circumferential directions by the bump lighting apparatus of the present invention, and an image of a solder bump thus lighted is captured by the bump image capturing apparatus according to the present invention under condition in which the intensity of reflected light lowered at least at the top portion of the solder bump. Since the quality of the state of the reinforcing resin applied to the solder bump is determined based on the image data captured in this manner by the image processing apparatus according to the present invention, the state of the reinforcing resin applied to the solder bump can be inspected well.

The bump inspecting apparatus may be constructed such that the circuit board has a plurality of solder bumps disposed on the surface thereof and that it further comprises a relative moving mechanism for moving the board holding mechanism relative to the irradiating mechanism and the image capture apparatus, and a central controller for integrally controlling the relative moving mechanism, the bump lighting apparatus, the bump image capturing apparatus and the image processing apparatus to successively light and capture an image of the solder bumps on the surface of the one circuit board to inspect the solder bumps.

In this case, the relative moving mechanism, bump lighting apparatus, bump image capturing apparatus and image processing apparatus are integrally controlled by the central controller so that the solder bumps on the surface of the one circuit board which is relatively moved by the relative moving mechanism are successively lighted by the bump lighting apparatus and captured by the bump image capturing apparatus and then inspected by the image processing apparatus. Since the state of the reinforcing resin applied is successively inspected for a large number of solder bumps disposed on the surface of the one circuit board, a large number of solder bumps of the one circuit board can be inspected automatically.

It is to be noted that the various means in the present embodiment are required only to be formed so as to implement the functions assigned thereto, and may be, for example, hardware for exclusive use, a computer to which suitable functions are provided by a program, functions implemented in the inside of a computer by an appropriate program, or a suitable combination of these.

An information storage medium according to the present invention stores a program therein for enabling a computer to execute a process of inputting image data of a spherical solder bump having a reinforcing resin applied to the lower half, mounted on the surface of a circuit board, a process of converting the inputted multilevel image data in binary form, a process of extracting the object corresponding to the portion of a solder bump exposed above the reinforcing resin from the binary image data, and a process of determining whether the extracted object is good or bad.

When the program stored in the information storage medium according to the present invention is read by a computer so that the computer may execute corresponding processes, the computer inputs image data of a spherical solder bump having a reinforcing resin applied to the lower half, mounted on the surface of a circuit board, and converts the inputted multilevel image data in binary form. Then, the computer extracts an object corresponding to the portion of a solder bump exposed above the reinforcing resin from the binary image data, and determines the quality of the extracted object. Consequently, the quality of the state of the reinforcing resin applied to the solder bump can be determined by the computer.

It is to be noted that the information recording medium in the present invention may be any medium on which a program for enabling a computer to execute various processes is stored in advance as software, and may be, for example, a ROM (Read Only Memory) or a HDD (Hard Disc Drive) fixed to an apparatus which includes a computer as a component, or a CD-ROM (Compact Disc ROM) or a FD (Floppy Disc) which is removably loaded into an apparatus which includes a computer as a component.

Further, the computer in the present invention may be any apparatus which can read a program of software and execute corresponding processing operation, and may be, for example, an apparatus which includes a CPU (Central Processing Unit) as a principal component and includes various devices such as a ROM, a RAM (Random Access Memory) and an I/F (Interface) connected to the CPU as necessary. In the present invention, to cause a computer to execute various operations corresponding to software may be to cause a computer to control operation of various devices.

The above and other objects, features and advantages according to the present invention will become apparent from the following description with reference to the accompanying drawings which illustrate examples according to the present invention.

DETAILED DESCRIPTION OF THE PREFERRED EMBODIMENTS

Figure 1:
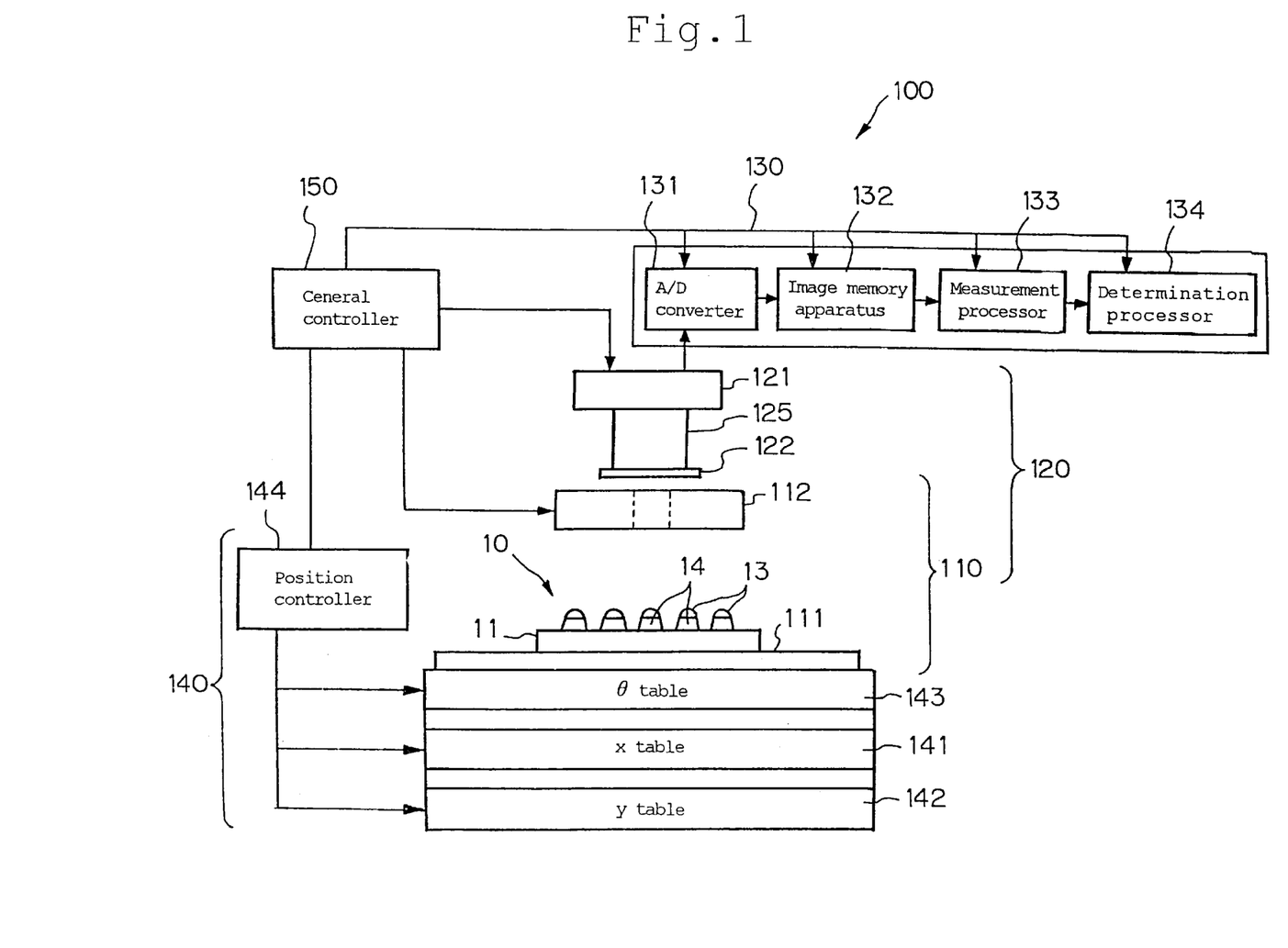
FIG. 1 is a schematic front elevational view showing a general construction of a bump inspecting apparatus according to an embodiment according to the present invention.

Referring now to FIG. 1, bump inspecting apparatus 100 according to an embodiment of the present invention includes bump lighting apparatus 110, bump image capturing apparatus 120, image processor 130, xyθ table 140 which serves as a relative moving mechanism, and central controller 150 which serves as a general controller, as principal components.

Figure 2:
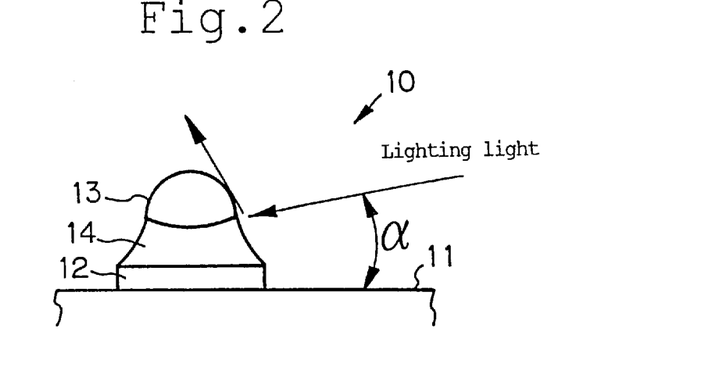
FIG. 2 is a side elevational view showing an outside shape of a solder bump of a circuit board as an object of inspection.

Circuit board 10 which is an object of inspection of bump inspecting apparatus 100 of the present embodiment has one board body 11, on the surface of which a large number of connection pads 12 are formed from printed wiring lines as shown in FIG. 2. A large number of solder bumps 13 are individually mounted on the surfaces of a large number of connection pads 12, and reinforcing resin 14 is applied to a lower half of each of a large number of solder bumps 13.

Figure 3A:
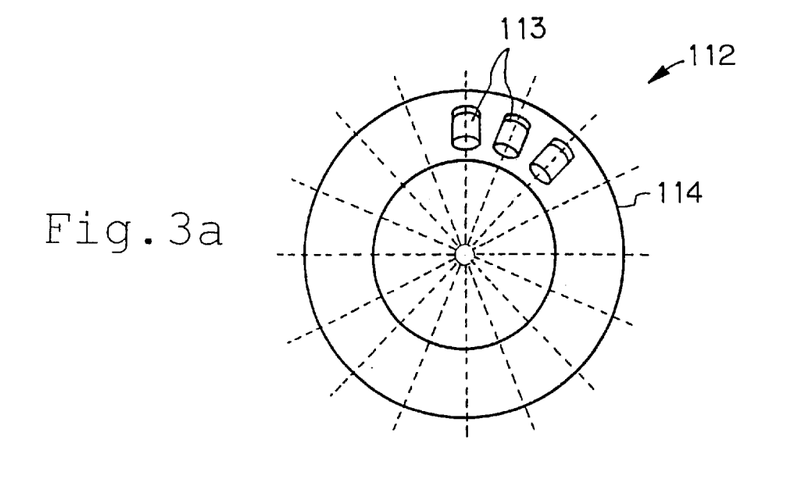
FIG. 3a is a plan view showing a bump lighting apparatus.
Figure 3B:
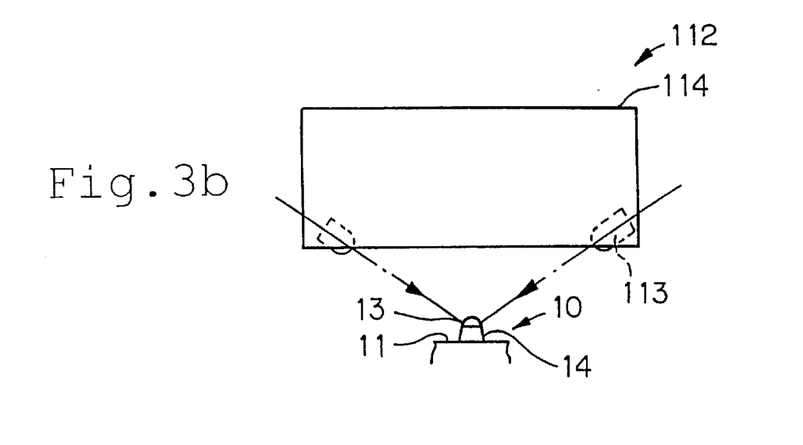
FIG. 3b is a side elevational view showing the bump lighting apparatus.

As shown in FIG. 1, bump lighting apparatus 110 includes board holding member 111 serving as a board carrying mechanism, and lighting unit 112 serving as an irradiating mechanism, as principal components. Lighting unit 112 includes, as shown in FIGS. 3a and 3b, a large number of LEDs (Light Emitting Diodes) 113 serving as light-emitting devices, and support frame 114 serving as a light source holding mechanism.

Board holding member 111 is formed as part of xyθ table 140 and holds circuit board 10 such that the surface of circuit board 10 on which solder bumps 13 are positioned may assume a horizontal position. Lighting unit 112 is disposed above board holding member 111 and lights a large number of solder bumps 13 on circuit board 10 one by one. More particularly, a large number of LEDs 113 are disposed radially inwardly in a horizontal plane as seen in FIG. 3a and in a downwardly inclined state in horizontal planes as seen in FIG. 3b by support frame 114 having an annular shape. Consequently, lighting unit 112 irradiates rays of light from all circumferential directions upon the outer periphery of solder bump 13 so that the rays of light may intersect at predetermined angle α of "5 to 15 degrees" with the surface of circuit board 10 held on board holding member 111 as seen in FIG. 2.

In the present embodiment, the surface of solder bump 13 in the condition of a mirror having a silver color, and the coloring of the surface of reinforcing resin 14 is blue. Since LEDs 113 emit rays of light of red of "0.66 ($\mu$m)", the rays of light emitted from LEDs 113 and the coloring of reinforcing resin 14 have a relationship of substantially complementary colors to each other.

Figure 4:
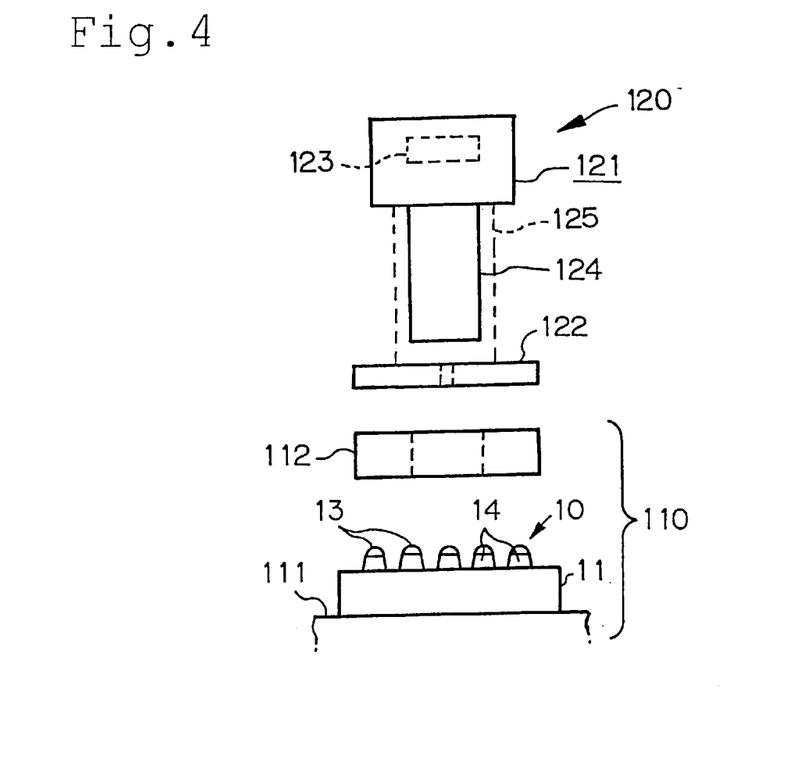
FIG. 4 is a front elevational view showing a bump image capturing apparatus.

Bump image capturing apparatus 120 has bump lighting apparatus 110 described above as an integral part and faces the surface of circuit board 10 from above. Bump image capturing apparatus 120 includes CCD (Charge Coupled Device) camera 121 serving as an image capturing apparatus and optical filter 122 as principal components. CCD camera 121 includes CCD array 123 and image forming optical system 124.

CCD camera 121 captures an image of reflected light from solder bump 13 lighted from bump lighting apparatus 110 with a predetermined dynamic range from a direction perpendicular to the surface of circuit board 10 to produce analog image data and outputs the analog image data to image processor 130.

Optical filter 122 is disposed in a gap between CCD camera 121 and solder bump 13 by barrel 125 serving as a filter disposing mechanism, and an intensity adjusting mechanism is provided by barrel 125 and optical filter 122.

Figure 5A:
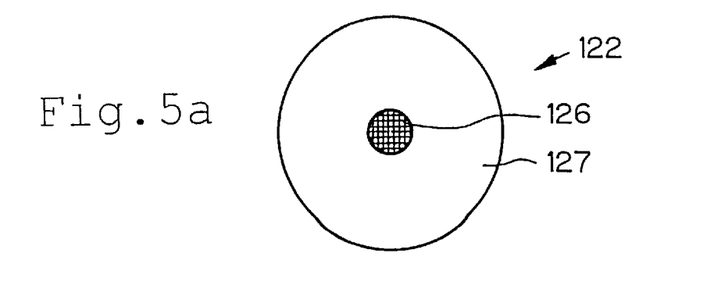
FIG. 5a is a plan view showing an optical filter.
Figure 5B:
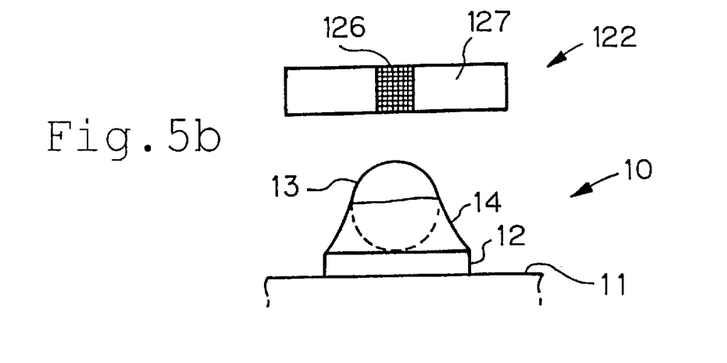
FIG. 5b is a front elevational view showing the optical filter.

Optical filter 122 has a disk-like shape corresponding to the shape of solder bump 13 in plan as seen in FIG. 5a and includes circular central portion 126 having a low transmittivity of approximately "30%", and annular outer circumferential portion 127 having a high transmittivity near to "100%". Central portion 126 of optical filter 122 having the low transmittivity has a diameter equal to substantially one half that of solder bump 13, and barrel 125 disposes optical filter 122 just above solder bump 13 as seen in FIG. 5b.

In short, optical filter 122 supported on barrel 125 reduces the intensity of reflected light from the central portion of solder bump 13 within the image capture range of CCD camera 121 until the intensity of reflected light from solder bump 13 to be imaged is adjusted to the dynamic range of CCD camera 121.

Image processor 130 is connected to bump image capturing apparatus 120 and processes image data of solder bump 13 captured by bump image capturing apparatus 120. Image processor 130 includes hardware components such as A/D converter 131 (Analog/Digital), image memory apparatus 132, measurement processor 133, and determination processor 134. Those apparatus 131 to 134 are connected in order.

A/D converter 131 converts analog image data captured by bump image capturing apparatus 120 into image data of digital multilevel, and image memory apparatus 132 temporarily stores the multilevel image data. Measurement processor 133 and determination processor 134 are formed from microcomputers, each of which includes hardware components such as, for example, a CPU, a ROM, a RAM, and an I/F (not shown).

In each of measurement processor 133 and determination processor 134, various control programs and process data are loaded in advance as software or firmware on an information medium such as the ROM or the RAM, and the CPU executes various data processes based on the software or firmware to logically implement various functions.

In particular, each of processors 133, 134 logically as a data setting function, a range limiting function, an image converting function and so forth and logically implements an object extracting function, a quality determining function, a process controlling function, and so forth.

The data setting function is such that the CPU sets predetermined data necessary for various image processes to the RAM. The predetermined data set in this manner include a circular window, a circumferential scanning position, a brightness offset value, an area tolerance, a ratio tolerance, and so forth.

Figure 6:
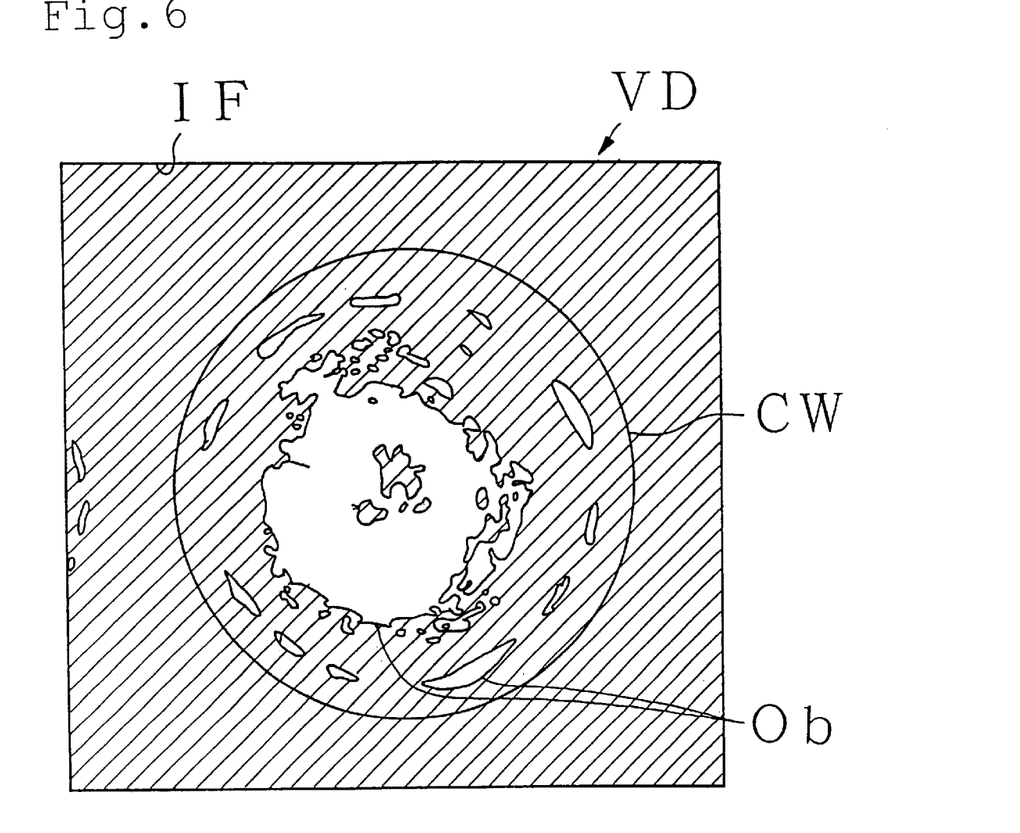
FIG. 6 is a schematic view illustrating image data of a solder bump.

As seen from FIG. 6, circular window CW is set as the processing range corresponding to the outside shape of solder bump 13 with respect to rectangular image capture frame IF of image data VD, and the circumferential scanning position is set as the start position from which scanning of a circumferentially inner portion of circular window CW is started.

The brightness offset value is set as a value with which a brightness obtained by scanning of the circumferentially inner portion of circular window CW is to be offset. The area tolerance is set as a tolerance for the area of object Ob extracted from image data VD. The ratio tolerance is set as a tolerance of the aspect ratio of object Ob and set to approximately "1.0±0.2".

The various data mentioned above can be registered as fixed values or default values in a control program if various pertaining parameters such as the diameter of solder bump 13 and the sensitivity of bump image capturing apparatus 120 are known in advance. Here, however, the control program is described so that desired values may be registered through a keyboard (not shown) by the user.

The range limiting function limits the processing range to a circular range corresponding to the outside shape of solder bump 13 as the CPU reads out the circular window whose data are set to the RAM as described above and the image data temporarily stored in image memory apparatus 132 and sets the circular window to the image data.

The image converting function has an average detecting function and a threshold value calculating function and converts the multilevel image data in binary form, whose processing range has been limited with the circular window described above, by predetermined data processing of the CPU corresponding to the control program loaded in the RAM.

More specifically, the average detecting function scans the circumferentially inner portion of the image data limited with the circular window from the circumferential scanning position mentioned hereinabove to detect an average brightness. The threshold value calculating function adds the aforementioned brightness offset value to the average brightness to calculate a slice level which is used as a threshold value for conversion. Consequently, the image converting function converts the multilevel image data in binary form with the slice level.

The object extracting function extracts an object corresponding to a portion of solder bump 13 exposed above reinforcing resin 14 from the binary image data in the circular window by predetermined data processing of the CPU corresponding to the control program loaded in the RAM.

The quality determining function has an area detecting function, an area comparing function, a ratio detecting function, a ratio comparing function and so forth, and determines whether the object is good or bad by predetermined data processing of the CPU corresponding to the control program loaded in the RAM.

More specifically, the area detecting function detects the area of the extracted object. The area comparing function compares the detected area of the object with the aforementioned area tolerance. The ratio detecting function detects the aspect ratio of the object whose detected area satisfies the tolerance. The ratio comparing function compares the detected aspect ratio with the aforementioned ratio tolerance.

When the ratio detecting function detects the aspect ratio of the object as described above, actually the center of gravity of the object is detected, and an inertial principal axis which is the major axis of the object is detected as the longest straight line which passes the center of gravity, whereafter the aspect ratio of the object is detected with the inertial principal axis set as a vertical axis.

When the object extracting function extracts the object from the image data in the circular window as described above, although the object which corresponds to the exposed portion of solder bump 13 ideally is one object, actually a plurality of objects are extracted while the image data in the circular window are successively scanned from a right upper portion to a left lower portion of the circular window.

Therefore, since the quality determining function successively inspects a plurality of objects corresponding to one solder bump 13, the process controlling function ends the processing of quality determination at the point in time when one good object is detected from among the plurality of objects by the predetermined data processing of the CPU corresponding to the control program loaded in the RAM.

xyθ table 140 includes x table 141 mounted for parallel movement in a horizontal x direction, y table 142 mounted for parallel movement in a horizontal y direction, and θ table 143 mounted for rotation in a horizontal θ direction. Tables 141 to 143 are placed one on another in this order.

Position controller 144 is connected to tables 141 to 143 and controls the positions of tables 141 to 143. Consequently, xyθ table 140 holds board body 11 held on board holding member 111 for movement and for rotation in horizontal directions.

General controller 150 is connected to various apparatus 110, 120, 130 and 140 described above and integrally controls operation of those apparatus 110, 120, 130 and 140. In short, since circuit board 10 has a large number of solder bumps 13 disposed on the surface thereof, central controller 150 integrally controls various apparatus 110 to 140 to successively light a large number of solder bumps 13 on the surface of circuit board 10 and capture images of solder bumps 13 to inspect solder bumps 13.

In the bump inspecting method by bump inspecting apparatus 100 of the present embodiment having the construction described above, circuit board 10 having a large number of solder bumps 13 disposed thereon with reinforcing resin 14 applied to solder bumps 13 is used as an object of inspection, and the applied states of reinforcing resin 14 to a large number of solder bumps 13 disposed on the surface of circuit board 10 are automatically inspected.

When an inspecting operation is performed by bump inspecting apparatus 100 in this manner, the user first sets various data corresponding to circuit board 10 to be inspected to image processor 130.

Figure 7:
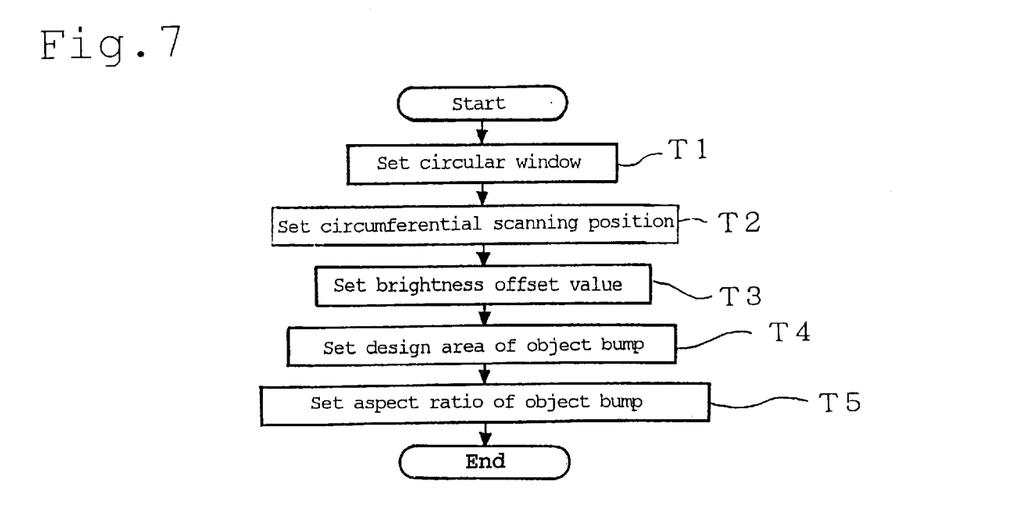
FIG. 7 is a flow chart illustrating processes when various data are set to the bump inspecting apparatus.

The various data include, for example, as indicated by steps T1 to T5 of FIG. 7, a circular window, a circumferential scanning position, a brightness offset value, an area tolerance and a ratio tolerance, and the data setting is executed by inputting operations of the keyboard corresponding to a guidance display on a display unit (not shown) of image processor 130.

When the data corresponding to circuit board 10 of the object of inspection are set to image processor 130 in this manner, bump inspecting apparatus 100 is enabled to execute an automatic inspecting operation.

Thus, circuit board 10 to be inspected is supplied to and held by board holding member 111 manually or automatically. Then, one of a large number of solder bumps 13 is moved to and stopped at an image capture position of bump image capturing apparatus 120 by xyθ table 140 whose operation is controlled by central controller 150.

In this state, one solder bump 13 is lighted by bump lighting apparatus 110, and an image of lighted solder bump 13 is captured by bump image capturing apparatus 120.

In the image capturing operation, according to the bump lighting method by bump lighting apparatus 110 of the present embodiment, rays of light which intersect at predetermined angle α with the surface of circuit board 10 as seen in FIGS. 2 and 3 are irradiated from the all circumferential directions upon an outer periphery of solder bump 13 with the intensity of approximately "40 $(mW/cm^2)$". Therefore, all positions on the boundary between the upper half of spherical solder bump 13 and reinforcing resin 14 are lighted substantially uniformly.

Where spherical solder bump 13 is lighted at a small angle from the all circumferential directions by bump lighting apparatus 110 in this manner, reflected light of a high intensity directed from a top portion of spherical solder bump 13 toward CCD camera 121 is less liable to appear. However, since a top portion of spherical solder bump 13 still acts as a plane perpendicular to the optical axis of CCD camera 121, reflected light of a high intensity appears at a central portion of solder bump 13 within the image capture range of CCD camera 121.

Therefore, according to the bump image capturing method by bump image capturing apparatus 120 of the present embodiment, when reflected light from solder bump 13 lighted in such a manner as described above is captured from a direction perpendicular to the surface of circuit board 10 by CCD camera 121, the intensity of reflected light at the central portion of solder bump 13 in the image capture range of CCD camera 121 is lowered by optical filter 122.

Consequently, since the intensity of rays of light reflected in a high density at a top portion of solder bump 13 whose spherical surface is formed as a mirror surface is lowered by optical filter 122 until it conforms with the dynamic range of CCD camera 121, CCD camera 121 captures an image of solder bump 13 without suffering from exposure to excessive light.

The image data captured by bump image capturing apparatus 120 in this manner are supplied to and processed by image processor 130. In image processor 130, the analog image data are converted into digital data by A/D converter 131, and the digital multilevel image data are temporarily stored into image memory apparatus 132.

Figure 8:
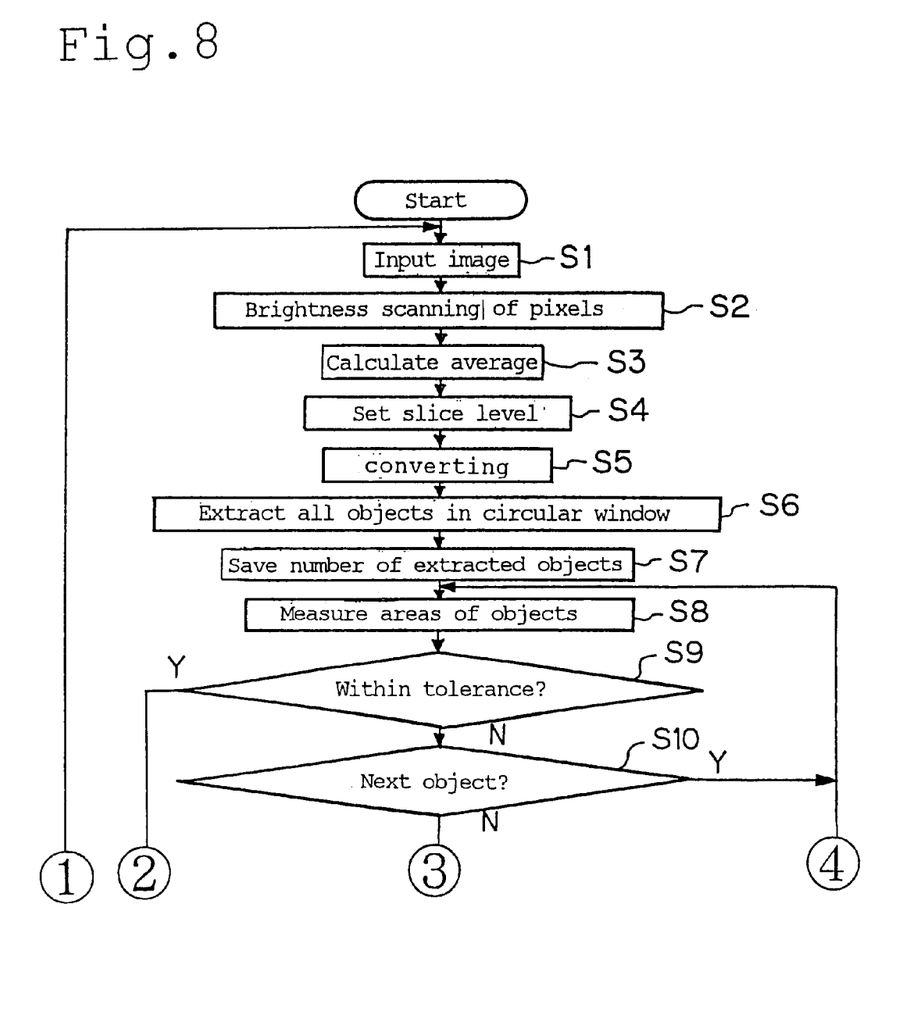
FIG. 8 is a flow chart illustrating the first half of processes in a bump inspecting method conducted with the bump inspection apparatus.

When image data of one of solder bumps 13 are inputted in step S1 of FIG. 8, the processing range of the image data is limited to a circular shape corresponding to the outside shape of solder bump 13 based on the set data of a circular window, and a circumferentially inward portion of the circular widow is scanned based on the set data of the circumferential canning position in step S2.

Since a captured image brightness of an outer periphery of solder bump 13 is detected as a result of the scanning, an average brightness value is calculated in step S3. Then in step S4, the brightness offset value is added to the average brightness value to calculate a slice level, and the multilevel image data are converted in binary form with the slice level in step S5.

Since the upper half of solder bump 13 exposed above reinforcing resin 14 is captured with a high intensity, the binary image data in the above manner, as shown in FIG. 6, shows a substantially circular object of a large size present at the center corresponding to the upper half of solder bump 13 and a plurality of deformed objects of small sizes which originate from noise are present around the circular object.

Thus, in step S6 of FIG. 8, the image data of one solder bump 13 is successively scanned to successively extract a plurality of objects, and in step S7, data of the number of objects is stored after the successive scanning of the internal region of the circular window is completed.

In step S8, the areas of the objects extracted in the manner described above are detected, and in step S9, the detected areas are compared with the set data of the area tolerance. However, since the plurality of objects have been detected as described above, the processing operation described above is successively executed in order for the plurality of objects until an object whose detected area satisfies the tolerance is detected.

If the processing operation comes to an end before an object whose detected area satisfies the tolerance is detected, then it is determined in steps S9 to S11 that solder bump 13 is bad and the detected areas and so forth are recorded together with identification data.

Figure 9:
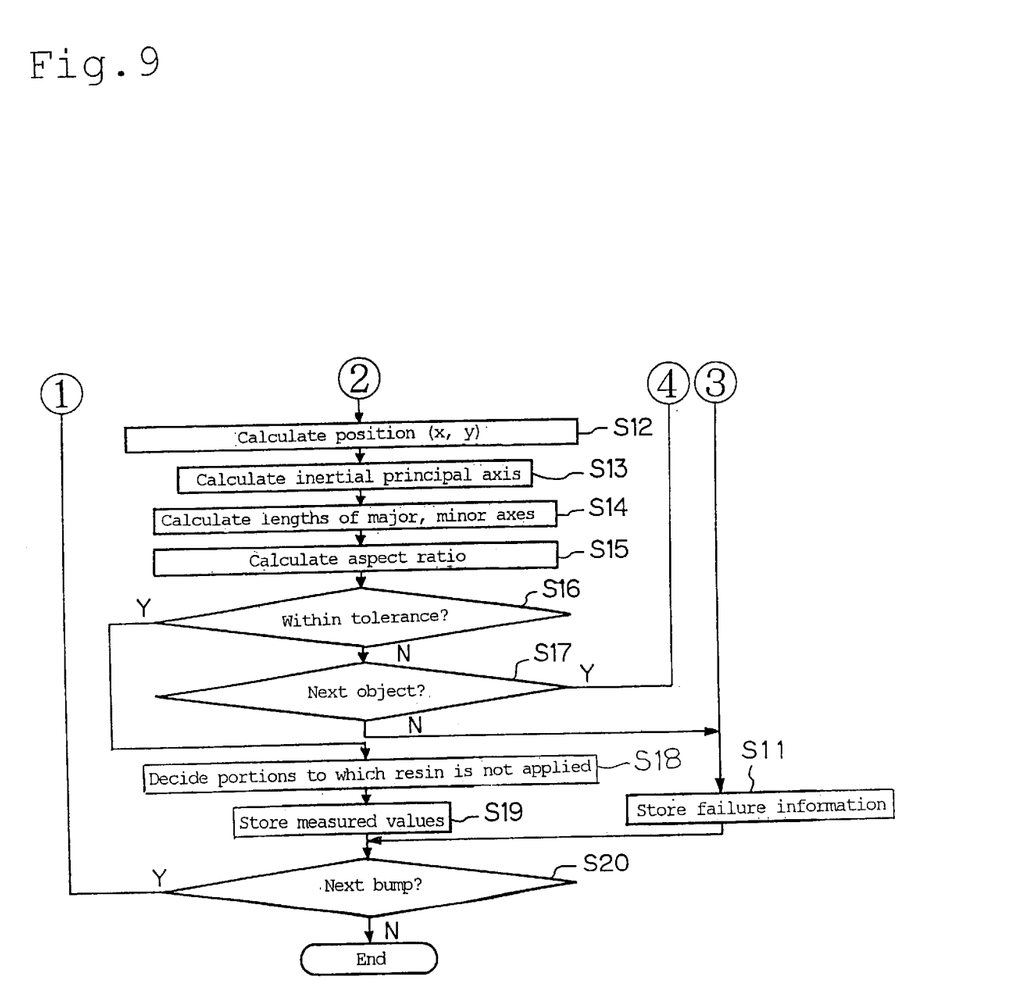
FIG. 9 is a flow chart illustrating the second half of processes in the bump inspecting method.

On the other hand, if an object whose detected area satisfies the tolerance is detected, then the confirmation processing of the detected areas described above is ended at that point of time, and confirmation processing of the aspect ratio is performed in steps S12 to S17.

In this case, the position of the center of gravity of the one object whose detected area satisfies the tolerance is calculated in step S12. In step S13, an inertial principal axis is detected as the longest straight line which passes the center of gravity. In steps S14 and S15, the aspect ratio is calculated with the inertial principal axis regarded as a vertical axis.

In step S16, the calculated aspect ratio is compared with the set data of the ratio tolerance. If the comparison reveals that the aspect ratio does not satisfy the tolerance, then the processing operation for area confirmation described above is repeated in steps S8 to S17.

If the processing operation comes to an end while an object whose detected area and aspect ratio satisfy the respective tolerances is not detected, then it is determined in step S11 that solder bump 13 in question is bad, and the aspect ratio and so forth are recorded together with identification data.

On the other hand, if an object whose detected area and aspect ratio satisfy the respective tolerances is detected, then it is determined in step S18 that this object is an object at an upper portion of solder bump 13 exposed above reinforcing resin 14. Then in step S19, the area, aspect ratio and so forth are recorded together with identification data of solder bump 13.

Since determination of the quality of the state of application of reinforcing resin 14 to the one solder bump 13 is completed with this, it is subsequently determined in step S20 whether there remains a next solder bump 13 or not.

If the next solder bump 13 is present, then the next solder bump 13 is moved to the image capture position of bump image capturing apparatus 120 by xyθ table 140 whose operation is controlled by central controller 150 as described above, and the processing operation described above is repeated for next the solder bump 13.

Since bump inspecting apparatus 100 of the present embodiment successively performs determination of the quality of the state of application of reinforcing resin 14 in order for each of a large number of solder bumps 13 of one circuit board 10 as described above, the quality of reinforcing resin 14 is automatically inspected for all of a large number of solder bumps 13 of one circuit board 10.

In short, since bump inspecting apparatus 100 eliminates the necessity for inspection of a great number of fine solder bumps 13 by visual observation, the yield of circuit boards 10 wherein solder bump 13 is reinforced with reinforcing resin 14 can be augmented.

Bump inspecting apparatus 100 of the present embodiment was produced experimentally and actually used to inspect a large number of solder bumps 13 of circuit board 10. The inspection proved that it was possible to inspect solder bumps 13 at a rate of one solder bump 13 in a short time of approximately "0.01 (sec)".

As described above, if a bad solder bump 13 is detected in the inspection, then identification data of this is recorded. Therefore, a bad solder bump can be specified readily from among a large number of fine solder bumps 13 disposed on the surface of circuit board 10.

Besides, since data of the area and the aspect ratio of a solder bump having been determined to be bad are also recorded, the recorded data can be referred to when the state of application of reinforcing resin 14 which has been determined to be bad is inspected closely.

Consequently, the cause of occurrence of a bad state of application of reinforcing resin 14 can be investigated readily, and an effective countermeasure can be taken rapidly. Therefore, the yield of circuit board 10 when it is produced in mass can be increased by eliminating design defects or defects of a production line.

Further, with bump inspecting apparatus 100 of the present embodiment, since the processing range of image data is first limited to a circular shape corresponding to the outside shape of solder bump 13 by a circular window, the range for which various processes should be performed can be limited to a minimum necessary range and the operation can be completed rapidly for the minimum necessary range.

Furthermore, since multilevel image data are converted in binary form with a slice level obtained by adding an offset value to an average brightness of the circumferentially inner portion of the circular window, the image data can be converted in binary form well into those of reinforcing resin 14 and those of solder bump 13.

Particularly since the light emission of bump lighting apparatus 110 and the coloring of reinforcing resin 14 satisfy a relationship of complementary colors to each other, reinforcing resin 14 can be represented well at a high density with image data, and the image data can be converted in binary form well into those of reinforcing resin 14 and those of solder bump 13.

Besides, although reinforcing resin 14 is applied to the outer periphery of each solder bump 13 which protrudes spherically, since bump inspecting apparatus 100 lights solder bump 13 from the all circumferential directions, the image data do not suffer from local deviation in brightness which would be otherwise caused by different lighting directions, and the image data can be converted in binary form well into the image data of reinforcing resin 14 and the image data of solder bump 13.

Furthermore, although reflected light of an extremely high intensity is likely to be captured at the position of the top of solder bump 13 which protrudes spherically, since the intensity of the rays of light at the center of solder bump 13 is lowered by optical filter 122, entire solder bump 13 can be imaged well by CCD camera 121, and image data which can be converted in binary form well can be produced.

Further, with bump inspecting apparatus 100 of the present embodiment, although a plurality of objects are extracted from image data of one solder bump 13, since the process of determination of the quality is ended at the point in time when one good object is detected from among the plurality of objects, the operation can be completed rapidly with minimized necessary processing for the plurality of objects.

The processing of determining the quality of an object involves comparison of the area and the aspect ratio of the object with the respective tolerances. Therefore, one object of a substantially circular shape and a large size corresponding to an exposed portion of solder bump 13 can be specified substantially with certainty, and wrong processing is not executed for a deformed object of a small size originating from noise. Particularly in detection of the aspect ratio, since an inertial principal axis which passes the center of gravity is used as the major axis, a deformed object originating from noise is prevented with certainty from being mistaken for a circular object.

In the embodiment described above, it is illustrated that, in order to light solder bump 13, which protrudes spherically, from all circumferential directions, a large number of LEDs 113 are arranged in inwardly radial directions on support frame 114 having an annular shape.

Figure 10:
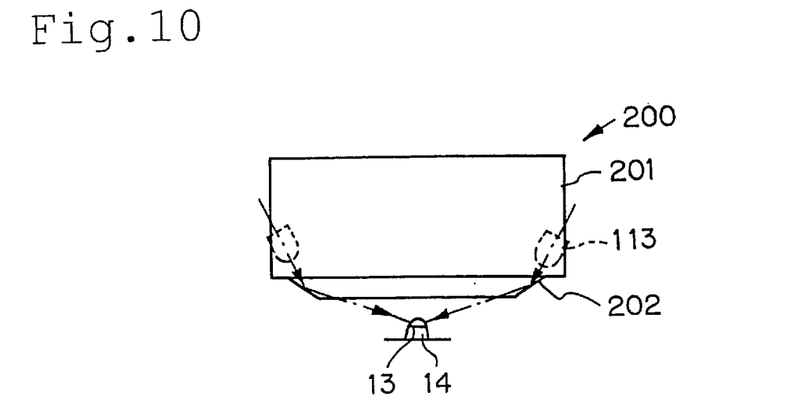
FIG. 10 is a front elevational view of a first modification to the bump lighting apparatus.
Figure 11:
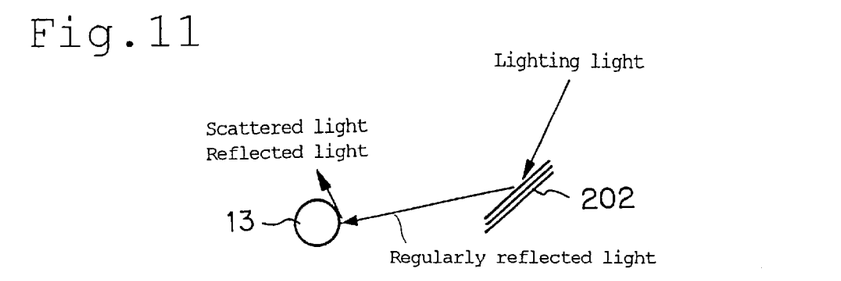
FIG. 11 is a schematic view of the essential part of the bump lighting apparatus of the first modification.

However, also bump lighting apparatus 200 illustrated in FIGS. 10 and 11 can possibly be used. In bump lighting apparatus 200, a large number of LEDs 113 are disposed in a substantially downwardly directed condition on support frame 201 of an annular shape, and rays of light emitted from a large number of LEDs 113 are diverted inwardly by polygon mirror 202, which is a light diverting mechanism mounted below support frame 201, so that they may be concentrated upon one point.

In this case, since each of a large number of LEDs 113 disposed circularly in a substantially downwardly directed condition on support frame 114 emits rays of light and those rays of light are diverted inwardly by polygon mirror 202 and concentrated upon one point, the outer periphery of solder bump 13 can be lighted from all circumferential directions with the rays of light.

Figure 12:
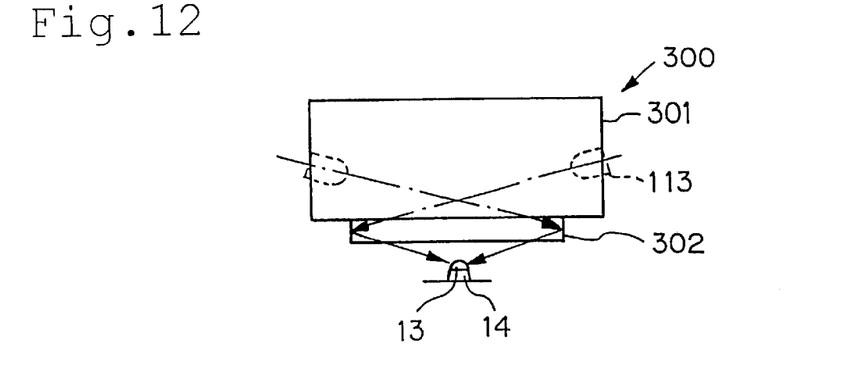
FIG. 12 is a front elevational view of a second modification to the bump lighting apparatus.
Figure 13:
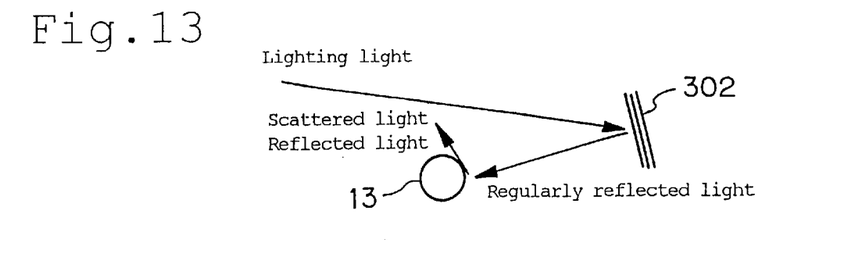
FIG. 13 is a schematic view of the essential part of the bump lighting apparatus of the second modification.

It is presumed that, with bump lighting apparatus 200 described above, a large number of LEDs 113 are arranged in a substantially downwardly directed condition on support frame 201 of an annular shape and polygon mirror 202 is arranged in a pyramid which is open upwardly. However, also bump lighting apparatus 300 illustrated in FIGS. 12 and 13 can possibly be used. In bump lighting apparatus 300, a large number of LEDs 113 are disposed in a substantially inwardly directed condition on support frame 301 of an annular shape, and polygon mirror 302 is arranged in a pyramid which is open downwardly.

Since bump lighting apparatus 200, 300 described above employ polygon mirror 202, 302, respectively, the number of parts increases and also the structure is complicated. However, since only polygon mirror 202, 302 is positioned around solder bump 13, disposition of and wiring to LEDs 113 are easy.

On the other hand, with bump lighting apparatus 110 described above, since polygon mirrors 202, 302 are not used, it is sometimes difficult to dispose a large number of LEDs 113 appropriately around solder bump 13 of a very small size, but the number of parts is small and the structure is simple. In short, since bump lighting apparatus 110, 200, 300 described above individually have different advantages and different disadvantages, preferably one of them is selected in accordance with required performances and specifications of an apparatus.

Further, in the embodiment described above, in order to prevent reflected light of an extremely high intensity at the position of the top of solder bump 13, optical filter 122 which has a lower transmittivity only at central portion 126 thereof is disposed in the gap between solder bump 13 and CCD camera 121.

Figure 14:
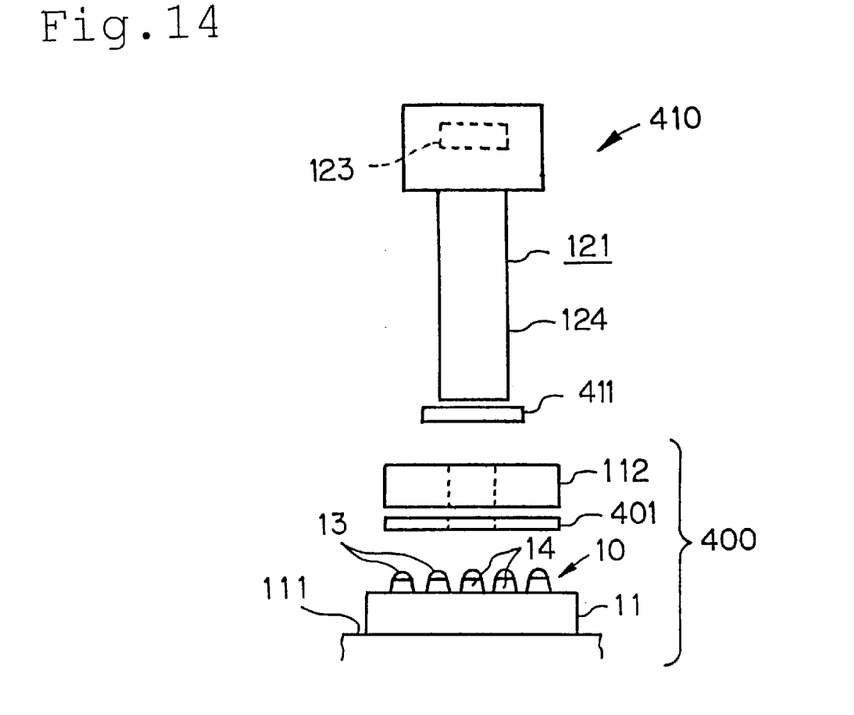
FIG. 14 is a front elevational view of a modification to the bump image capturing apparatus.
Figure 15:
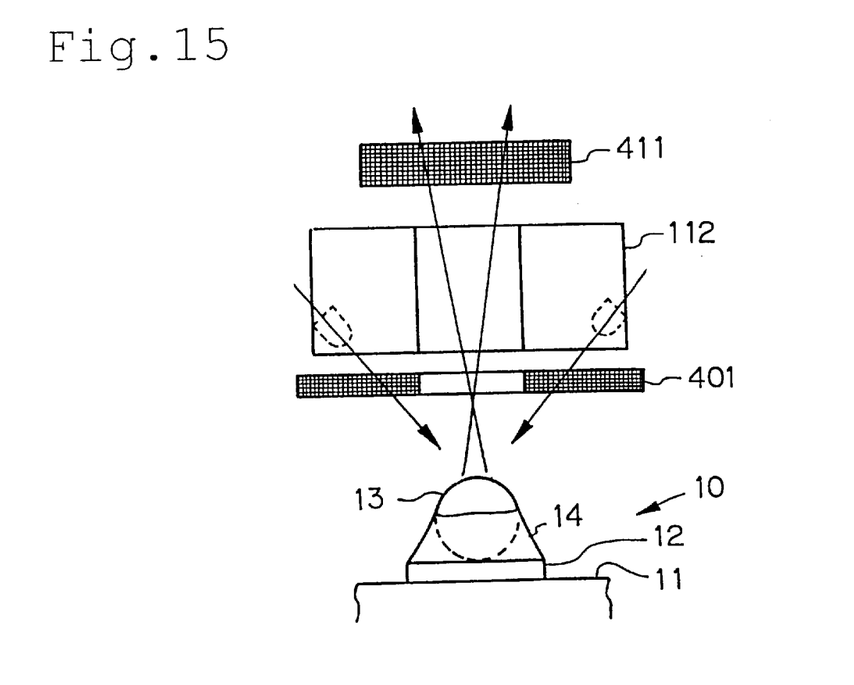
FIG. 15 is a schematic view of the essential part of the bump image capturing apparatus of the modification.

However, also such an alternative arrangement as in bump lighting apparatus 400 and bump image capturing apparatus 410 illustrated in FIGS. 14 and 15, respectively, can possibly be used. In bump lighting apparatus 400 and bump image capturing apparatus 410, lighting polarizing filter 401 serving as a first light converting member is disposed in the gap between lighting unit 112 and solder bump 13, and image capture polarizing filter 411 serving as a second light converting member is disposed in the gap between solder bump 13 and CCD camera 121.

In this case, rays of light to be irradiated upon solder bump 13 from bump lighting apparatus 400 are converted into polarized light by lighting polarizing filter 401, and rays of light reflected by solder bump 13 and used to be imaged by CCD camera 121 are converted into polarized light by image capture polarizing filter 411. Consequently, the intensity of rays of light reflected in a high intensity at a top portion of solder bump 13 whose surface is formed as a mirror surface is reduced to a level suitable for image capture.

Further, while, in the embodiment described above, image data in the inside of a circular window are successively scanned in directions of rows and columns to extract a plurality of objects, it is otherwise possible, for example, to execute image scanning for extraction of an object spirally outside shape the center of the circular window to extract one object from the image data at a central portion of the circular window.

In this case, since one object is extracted from the image data at a central portion of the circular window, an object at a portion of solder bump 13 exposed above reinforcing resin 14 can be extracted at one time. Consequently, the operation of extracting an object can be completed very rapidly.

Furthermore, while, in the embodiment described above, the components of image processor 130 are individually formed from hardware elements for exclusive use, it is otherwise possible, for example, to implement the components of image processor 130 by incorporating suitable software into a computer so that the computer may operate based on the software or to implement some of the components with software and form the others of the components from hardware.

Where the components of image processor 130 are implemented with software as described above, a program for causing a CPU of the computer to execute such operations as to input image data of spherical solder bump 13 which is mounted on the surface of circuit board 10 and has reinforcing resin 14 applied to the lower half thereof, converted the inputted multilevel image data in binary form, extract, from within the binary image data, an object corresponding to a portion of solder bump 13 exposed above reinforcing resin 14 and determine the quality of the extracted object should be stored on a computer-readable information storage medium such as a RAM.

While preferred embodiments according to the present invention have been described using specific terms, such description is for illustrative purposes only, and it is to be understood that changes and variations may be made without departing from the spirit or scope of the following claims.

What is claimed is:

1. An image processing apparatus comprising:
    image converting means for converting multilevel image data of a spherical solder bump into binary form, said bump having a reinforcing resin applied to the lower half, mounted on the surface of a circuit board;
    object extracting means for extracting an object corresponding to the portion of a solder bump exposed above the reinforcing resin from the binary image data by said image converting means; and
    quality determining means for determining whether the object extracted by said object extracting means is good or bad,
    said quality determining means including:
        ratio detecting means for detecting the aspect ratio of the object extracted by said object extracting means; and
        ratio comparing means for comparing the aspect ratio detected by said ratio detecting means with a predetermined tolerance.

2. An image processing apparatus according to claim 1, further comprising
    range limiting means for limiting a processing range of the image data to a circular shape corresponding to the outside shape of a solder bump.

3. An image processing apparatus according to claim 2, wherein said image converting means includes:
    average detecting means for detecting an average brightness of the image data in the circumferentially inward portion of the circle limited by said range limiting means; and
    threshold value calculating means for adding a predetermined offset value to the average brightness detected by said average detecting means to calculate a threshold value for conversion.

4. An image processing apparatus according to claim 1, further comprising
    process controlling means for controlling at least the processing operation of said quality determining means, and wherein:
        said object extracting means includes means for successively scanning the image data of one solder bump to successively extract a plurality of objects;
        said quality determining means includes means for successively inspecting the plurality of objects corresponding to the one solder bump; and
        said process controlling means includes means for completing the processing of said quality determining means at the point in time when one good object is detected from among the plurality of objects.

5. An image processing apparatus according to claim 1, wherein said object extracting means includes means for extracting one object from the image data at a central portion.

6. An image processing apparatus according to claim 1, wherein said quality determining means includes:
    area detecting means for detecting the area of the object extracted by said object extracting means; and
    area comparing means for comparing the area detected by said area detecting means with a predetermined tolerance.

7. An image processing apparatus according to claim 1, wherein said ratio detecting means includes means for detecting the major axis of the object extracted by said object extracting means and using the detected major axis of the object as a vertical axis.

* * * * *